United States Patent [19]

Krämer et al.

[11] 4,366,152

[45] Dec. 28, 1982

[54] COMBATTING FUNGI WITH METAL SALT COMPLEXES OF 1-PHENYL-2-(1,2,4-TRIAZOL-1-YL)-ETHANES

[75] Inventors: Wolfgang Krämer; Helmut Timmler; Karl H. Büchel, all of Wuppertal; Wilhelm Brandes, Leichlingen; Paul-Ernst Frohberger; Hans Scheinpflug, both of Leverkusen, all of Fed. Rep. of Germany

[73] Assignee: Bayer Aktiengesellschaft, Leverkusen, Fed. Rep. of Germany

[21] Appl. No.: 909,602

[22] Filed: May 25, 1978

[30] Foreign Application Priority Data

Jun. 3, 1977 [DE]  Fed. Rep. of Germany ....... 2725214

[51] Int. Cl.³ ............... A01N 55/02; A01N 55/04; C07D 249/08; C07F 1/08
[52] U.S. Cl. .................. 424/245; 424/269; 548/101; 548/262; 542/413; 542/427
[58] Field of Search .................. 260/308 R, 299; 424/269, 245; 542/413, 427; 548/101, 262

[56] References Cited

U.S. PATENT DOCUMENTS 4,005,083  1/1977  Büchel et al. .................. 260/299
4,073,901  2/1978  Büchel et al. .................. 260/308 R

FOREIGN PATENT DOCUMENTS 2547953  4/1977  Fed. Rep. of Germany ... 260/308 R

*Primary Examiner*—Alton D. Rollins
*Attorney, Agent, or Firm*—Sprung, Horn, Kramer & Woods

[57] ABSTRACT

Combating fungi with metal salt complexes of 1-phenyl-2-(1,2,4-triazol-1-yl)-ethanes of the formula

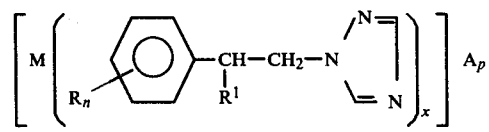

in which R represents halogen, alkyl, alkoxy, alkylthio, alkylsulphonyl, halogenoalkyl, nitro, cyano, optionally substituted phenyl or optionally substituted phenoxy, $R^1$ represents the grouping $-O-R^2$, $-S(O)_m-R^3$ or $-O-CO-R^4$, $R^2$ represents alkyl, alkenyl, alkynyl, cycloalkyl, optionally substituted aryl, optionally substituted araylalkyl or optionally substituted arylalkenyl, $R^3$ represents hydrogen, alkyl, alkenyl, alkynyl, cycloalkyl, optionally substituted aryl, optionally substituted arylalkyl or optionally substituted arylalkenyl, $R^4$ represents alkyl, alkenyl, alkynyl, cycloalkyl, optionally substituted aryl, optionally substituted arylalkyl, optionally substituted arylalkenyl, halogenoalkyl, optionally substituted phenoxyalkyl, amino, alkylamino, dialkylamino, alkyl-alkylcarbonylamino or optionally substituted phenylamino, A represents an anion of an inorganic acid,
M represents a metal,
n represents 0, 1, 2, 3, 4 or 5,
m represents 0, 1 or 2,
p represents 1, 2, 3, 4, 5 or 6, and
x represents 1, 2, 3 or 4 which possess fungicidal properties.

10 Claims, No Drawings

COMBATTING FUNGI WITH METAL SALT COMPLEXES OF 1-PHENYL-2-(1,2,4-TRIAZOL-1-YL)-ETHANES

The present invention relates to and has for its objects the provision of particular new metal salt combating fungi with metal salt complexes of 1-phenyl-2-(1,2,4-triazol-1-yl)-ethanes which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It has already been disclosed that certain 1-[β-aryl-β-(R-oxy)-ethyl]-imidazoles, for example 1-[β-butoxy-β-(4'-chlorophenyl)-ethyl]-imidazole, and 1-[β-aryl-β-(R-oxy)-ethyl]-triazoles, for example 1-[β-allyloxy-β-(4'-chlorophenyl)-ethyl]-1,2,4-triazole, have a good fungicidal activity (see German Offenlegungsschriften (German Published Specifications) Nos. 2,063,857 and 2,640,823). However, their action in certain fields of indication, in particular when low amounts and concentrations are used, is not always completely satisfactory. Furthermore, it has been generally known for a relatively long time that zinc ethylene-1,2-bis-dithiocarbamidate is a good agent for combating fungal plant diseases (see Phytopathology 33, 1113 (1963)). However, its use as a seed dressing is only possible to a limited extent since it exhibits little activity when low amounts and concentrations are used.

The present invention now provides, as new compounds, the metal salt complexes of 1-phenyl-2-triazolyl-ethyl derivatives, of the general formula

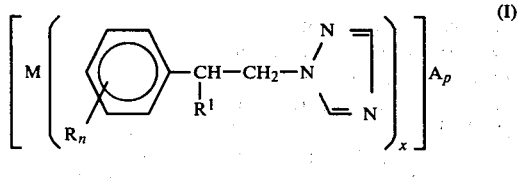

in which

R represents halogen, alkyl, alkoxy, alkylthio, alkylsulphonyl, halogenoalkyl, nitro, cyano, optionally substituted phenyl or optionally substituted phenoxy, $R^1$ represents the grouping $-O-R^2$, $-S(O)_m-R^3$ or $-O-CO-R^4$, $R^2$ represents alkyl, alkenyl, alkynyl, cycloalkyl, optionally substituted aryl, optionally substituted arylalkyl or optionally substituted arylalkenyl, $R^3$ represents hydrogen, alkyl, alkenyl, alkynyl, cycloalkyl, optionally substituted aryl, optionally substituted arylalkyl or optionally substituted arylalkenyl, $R^4$ represents alkyl, alkenyl, alkynyl, cycloalkyl, optionally substituted aryl, optionally substituted arylalkyl, optionally substituted arylalkenyl, halogenoalkyl, optionally substituted phenoxyalkyl, amino, alkylamino, dialkylamino, alkyl-alkylcarbonylamino or optionally substituted phenylamino, A represents an anion of an inorganic acid, M represents a metal, n represents 0, 1, 2, 3, 4 or 5, m represents 0, 1, or 2, p represents 1, 2, 3, 4, 5 or 6 and x represents 1, 2, 3 or 4.

The compounds of this invention have powerful fungicidal properties.

Preferably, R represents halogen (especially fluorine, chlorine or bromine), nitro, cyano, alkyl with 1 to 4 carbon atoms, alkylsulphonyl with 1 to 4 carbon atoms, alkoxy with 1 or 2 carbon atoms, alkylthio with 1 or 2 carbon atoms, halogenoalkyl with up to 4 carbon atoms and up to 5 halogen atoms (especially with up to 2 carbon atoms and up to 3 identical or different halogen atoms, preferred halogen atoms being fluorine and chlorine, and an example of such halogenoalkyl being trifluoromethyl), or phenyl or phenoxy either of which may optionally carry one or more substituents selected from halogen (especially fluorine, chlorine and bromine), cyano, nitro and halogenoalkyl with up to 2 carbon atoms and up to 3 identical or different halogen atoms (preferred halogen atoms being fluorine and chlorine, and an example of such halogenoalkyl being trifluoromethyl);

n represents 0, 1, 2 or 3;

$R^1$ represents $-O-R^2$, $-S(O)_m-R^3$ or $-O-CO-R^4$;

$R^2$ represents alkyl, alkenyl or alkynyl with up to 4 carbon atoms in each case, cycloalkyl with 5 to 7 carbon atoms, aryl with 6 to 10 carbon atoms or arylalkyl or arylalkenyl each with 6 to 10 carbon atoms in the aryl part and up to 4 carbon atoms in the alkyl or alkenyl part (for example phenyl, naphthyl, benzyl, naphthylmethyl and styryl), the three last-mentioned groups optionally being substituted by halogen (especially fluorine, chlorine or bromine), cyano, nitro, amino, alkyl with 1 to 4 carbon atoms, halogenoalkyl with up to 2 carbon atoms and up to 3 identical or different halogen atoms (preferred halogen atoms being fluorine and chlorine, as in, for example, trifluoromethyl) or phenoxy which is itself optionally substituted by halogen (especially fluorine or chlorine);

$R^3$ represents hydrogen, alkyl, alkenyl or alkynyl with up to 4 carbon atoms in each case, cycloalkyl with 5 to 7 carbon atoms, aryl with 6 to 10 carbon atoms or arylalkyl or arylalkenyl each with 6 to 10 carbon atoms in the aryl part and up to 4 carbon atoms in the alkyl or alkenyl part (for example phenyl, naphthyl, benzyl, naphthylmethyl and styryl), the three last-mentioned groups optionally being substituted by halogen (especially fluorine, chlorine or bromine), cyano, nitro, amino, alkyl with 1 to 4 carbon atoms, halogenoalkyl with up to 2 carbon atoms and up to 3 identical or different halogen atoms (preferred halogen atoms being fluorine and chlorine, as in, for example, trifluoromethyl) or phenoxy which is itself optionally substituted by halogen (especially fluorine or chlorine);

$R^4$ represents alkyl, alkenyl or alkynyl with up to 4 carbon atoms in each case, cycloalkyl with 5 to 7 carbon atoms, aryl with 6 to 10 carbon atoms or arylalkyl or arylalkenyl each with 6 to 10 carbon atoms in the aryl part and up to 4 carbon atoms in the alkyl or alkenyl part (for example phenyl, naphthyl, benzyl, naphthylmethyl and styryl), the three last-mentioned groups optionally being substituted by halogen (especially fluorine, chlorine or bromine), cyano, nitro, amino, alkyl with 1 to 4 carbon atoms, halogenoalkyl with up to 2 carbon atoms and up to 3 identical or different halogen atoms (preferred halogen atoms being fluorine and chlorine, as in, for example, trifluoromethyl) or phenoxy which is itself optionally substituted by halogen (especially fluorine or chlorine), or $R^4$ represents halogenoalkyl with 1 to 2 carbon atoms and 1 to 5 halogen atoms (especially fluorine and chlorine, as in, for example, trifluoromethyl, dichloromethyl and chloromethyl) or phenoxyalkyl which has 1 or 2 carbon atoms in the alkyl part and which is optionally substituted in the phenyl part by halogen (especially fluorine or chlorine), amino, cyano, nitro or alkyl with 1 to 2 carbon atoms, or $R^4$ represents amino, alkylamino, dialkylamino or alkylalkylcarbonylamino each with 1 to 4 (especially 1 to 2) carbon atoms in each alkyl part or phenylamino which is optionally substituted by halogen (especially fluorine or chlorine), nitro and cyano;

M represents a metal selected from the main groups II to IV and sub-groups I and II and IV to VIII (for example copper, zinc, manganese, magnesium, tin, iron and nickel);

A represents a nitrate, sulphate or phosphate anion or a halide such as chloride, bromide or iodide, which anion may be in hydrated form; and p represents 1, 2, 3 or 4.

The invention also provides a process for the preparation of a metal complex of the formula (I) in which a 1-phenyl-2-triazolyl-ethyl derivative of the general formula

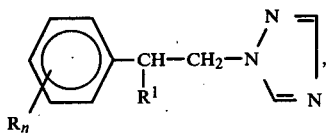
(II)

in which

R, $R^1$ and n have the meanings stated above, is reacted with a metal salt of the general formula

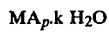 (III), in which k represents a number from 0 to 12 (especially 0 to 8) and M, A and p have the meanings stated above, in the presence of a diluent.

Surprisingly, the metal complexes, according to the invention, of 1-phenyl-2-triazolyl-ethyl derivatives exhibit a considerably higher fungicidal activity, in particular against species of rust and mildew, than the 1-[β-aryl-β-(R-oxy)-ethyl]-imidazoles and -triazoles known from the state of the art, for example 1-[β-butoxy-β-(4'-chlorophenyl)-ethyl]-imidazole, which are closely related substances chemically and from the point of view of their action, and than zinc ethylene-1,2-bis-dithiocarbamidate, which is a known substance having the same type of action. The active compounds according to the invention thus represent an enrichment of the art.

If 1-(2,4-dichlorophenyl)-2-(1,2,4-triazol-1-yl)-ethyl allyl ether and copper(II) chloride are used as starting materials, the course of the reaction can be represented by the following equation:

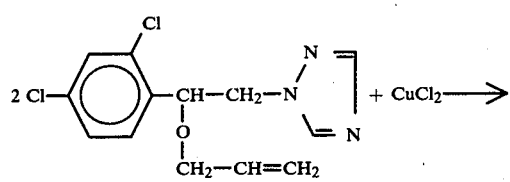

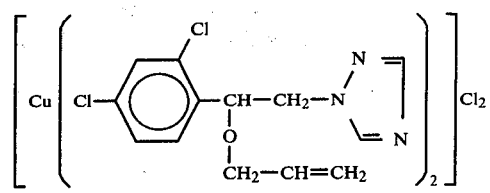

Some of the starting materials of the formula (II) are known (see U.S. Ser. No. 729,935, filed Oct. 6, 1976, now U.S. Pat. No. 4,327,104) and DT-OS (German Published Specification) No. 2,640,823, and some of them are the subject of U.S. Ser. No. 804,832, filed June 8, 1977 and U.S. Ser. No. 833,926, filed Sept. 16, 1977. Starting materials of the formula (II) can be obtained by processes described in the literature, for example by (a) reacting alkanolates of 1-hydroxy-1-phenyl-2-triazolylethane derivatives, of the general formula

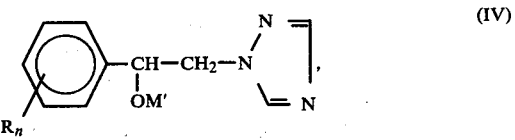
(IV)

in which

R and n have the meanings stated above and

M' represents an alkali metal, preferably lithium, sodium or potassium, or a quaternary ammonium or phosphonium group, with a halide of the general formula

Hal—$R^1$ (V), in which $R^1$ has the meaning stated above and

Hal represents chlorine or bromine, in the presence of an organic solvent, for example dioxane or chloroform, at temperatures between 20° and 120° C. In order to isolate the end products, the reaction mixture is freed from the solvent, and water and an organic solvent are added to the residue. The organic phase is separated off, worked up in the customary manner and purified.

In a preferred embodiment, the procedure is to use a 1-hydroxy-1-phenyl-2-triazolyl-ethane derivative as the starting material, to convert this into the alkali metal alcoholate of the formula (IV) in a suitable inert solvent by means of an alkali metal hydride or alkali metal amide and to react the alcoholate immediately, without isolation, with a halide of the formula (V), the compound of the formula (II) being obtained in one operation with the elimination of the alkali metal halide.

According to another preferred embodiment, the preparation of the alkanolate of the formula (IV) and the reaction with the halide of the formula (V) are appropriately carried out in a two-phase system, for example aqueous sodium hydroxide solution or potassium hydroxide solution/toluene or methylene chloride, a phase transfer catalyst, such as, for example, an ammonium or phosphonium compound, being added.

The starting materials of the formula (II) can also be obtained when (b) the 1-hydroxy-1-phenyl-2-triazolyl-ethanes on which the alklanolates of the formula (IV) are based (i) are reacted with appropriate acid anhydrides by known methods, for example in equimolar amounts in the presence of an inert organic solvent, for example acetone, or with an excess of acid anhydride and in the presence of an acid or basic catalyst, for example sodium acetate, at temperatures between 0° and 150° C. and the compounds of the formula (II) are isolated in the customary manner, or (ii) are reacted with appropriate isocyanates by known methods, for example in equimolar amounts in the presence of an inert organic solvent, for example benzene, and in the presence of a catalyst, for example dibutyl-tin dilaurate, at temperatures between 0° and 100° C. and the compounds of the formula (II) are isolated in the customary manner, or (c) 1-halogeno-1-phenyl-2-triazolyl-ethanes of the general formula

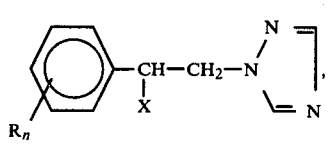

in which

R and n have the meanings stated above and

X represents halogen, are reacted with mercaptans of the general formula

        (VII), in which $R^3$ has the meaning stated above, in a known manner in the presence of an inert organic solvent, for example acetone, and in the presence of an acid-binding agent, for example potassium carbonate, at temperatures between 60° and 100° C., and the thioethers thereby obtained are optionally oxidized in a manner which is in itself known at temperatures between −30° and +80° C. using inorganic or organic oxidizing agents, for example m-chloroperbenzoic acid or potassium permanganate. The compounds of the formula (II) are isolated in the customary manner.

The 1-hydroxy-1-phenyl-2-triazolyl-ethane derivatives on which the alkanolates of the formula (IV) are based are known (see U.S. Ser. No. 792,756, filed May 2, 1977 and U.S. Ser. No. 729,935, filed Oct. 6, 1976, now U.S. Pat. No. 4,327,104.

The 1-halogeno-1-phenyl-2-triazolyl-ethane derivatives of the formula (VI) are also known (see U.S. Ser. No. 729,930, filed Oct. 6, 1976, now U.S. Pat. No. 4,102,891.

Examples of the 1-phenyl-2-triazolyl-ethyl derivatives of the formula (II) to be used according to the invention as starting materials are given in the following Tables 1, 2 and 3:

TABLE 1

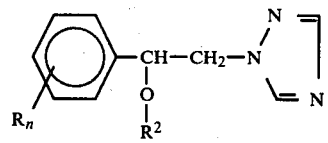

| $R_n$ | $R^2$ | Melting point (°C.) or refractive index |
|---|---|---|
| 2,4-Cl$_2$ | —CH$_2$—⟨Cl,Cl⟩ | 84 |
| 2,4-Cl$_2$ | —CH$_2$—CH=CH$_2$ | $n_D^{20}$ = 1.545 |
| 2,4-Cl$_2$ | —CH$_2$—C≡CH | 130 (decomposition) × HNO$_3$) |
| 4-Cl | —CH$_2$—⟨Cl,Cl⟩ | 78 |
| 4-Cl | —CH$_2$—⟨Cl⟩ | 111 |
| 2,4-Cl$_2$ | —CH$_2$—⟨Cl⟩ | 120 |
| 4-Cl | —CH$_2$—⟨Cl,Cl⟩ | 118 |
| 4—⟨⟩—Cl | —CH$_2$—CH=CH$_2$ | 225 (decomposition) (× ½ NDS) |
| 4-O—⟨⟩ | —CH$_2$—CH=CH$_2$ | $n_D^{22}$ = 1.570 |
| 4-O—⟨⟩—Cl | —CH$_2$—⟨Cl,Cl⟩ | 200 (× ½ NDS) |
| 4-O—⟨⟩—Cl | —CH$_2$—CH=CH$_2$ | 213 (× ½ NDS) |
| 2,4-Cl$_2$ | —⟨⟩—NO$_2$ | 174 (decomposition) (× HNO$_3$) |
| 2,4-Cl$_2$ | —⟨⟩—NH$_2$ | 124 (decomposition) (× ½ HNO$_3$) |
| 4-O—⟨⟩ | —CH$_2$—⟨Cl,Cl⟩ | 145 (decomposition) (× ½ NDS) |
| 2,4-Cl$_2$ 4-Br | CH$_3$ —CH$_2$—CH=CH$_2$ | 143–46 (× HCl) 193 (× ½ NDS) |
| 4—⟨⟩—Cl | —CH$_2$—⟨Cl,Cl⟩ | 237 (× ½ NDS) |

TABLE 1-continued

Structure (IIa):

Ar(Rn)-CH(OR²)-CH₂-N(triazole)

| Rn | R² | Melting point (°C.) or refractive index |
|---|---|---|
| 4-O-C₆H₅ | -CH₂-C₆H₄-Cl | 90 |
| 4-O-C₆H₅ | -CH₂-(2,3-Cl₂-C₆H₃) | 124 |
| 4-O-(4-Cl-C₆H₄) | CH₃ | 211 (decomposition) (× ½ NDS) |
| 4-O-C₆H₅ | -CH₂-C≡CH | 158 (decomposition) (× ½ NDS) |
| 4-Br | -CH₂-(2,4-Cl₂-C₆H₃) | 76 |
| 4-Cl | -CH₂-CH=CH₂ | 140 (× HCl) |
| 4-O-(4-Br-C₆H₄) | -CH₂-(2,4-Cl₂-C₆H₃) | viscous oil |
| 4-O-(4-Br-C₆H₄) | -CH₂-CH=CH₂ | viscous oil |
| 4-O-(4-Br-C₆H₄) | -CH₂-C₆H₄-Cl | 135 |
| 2,4-Cl₂ | -CH₂-C₆H₄-Cl | 108 |
| 2,4-Cl₂ | C₄H₉ | viscous oil |
| 2,4-Cl₂ | -CH₂-(2,4-Cl₂-C₆H₃) | 89-91 |
| 2,4-Cl₂ | -CH₂-C₆H₄-NO₂ | 105 |
| 4-Br | -CH₂-(2,3-Cl₂-C₆H₃) | 138 |
| 4-O-(4-Br-C₆H₄) | -CH₂-(2,3-Cl₂-C₆H₃) | 189 (× HCl) |
| 4-Br | -CH₂-C₆H₄-Cl | 102 |
| 4-(4-Cl-C₆H₄) | -CH₂-(2,3-Cl₂-C₆H₃) | 165 |
| 2,4-Cl₂ | -CH₂-C₆H₄-Cl | 107 |
| 2,4-Cl₂ | -CH₂-C(CH₃)=CH₂ | viscous oil |
| 4-(4-Cl-C₆H₄) | -CH₂-C₆H₄-Cl | 103 |
| 4-O-(4-Cl-C₆H₄) | -CH₂-C₆H₄-Cl | 136 |
| 4-O-(4-Cl-C₆H₄) | -CH₂-(2,3-Cl₂-C₆H₃) | 98 |
| 4-O-(4-Cl-C₆H₄) | -CH₂-C(CH₃)=CH₂ | 185 (decomposition) (× ½ NDS) |
| 4-O-(4-Cl-C₆H₄) | -CH₂-C≡CH | viscous oil |
| 4-O-(4-Cl-C₆H₄) | -CH₂-C₆H₄-Cl | 212 (× ½ NDS) |
| 4-O-(4-Cl-C₆H₄) | -CH₂-(2,3-Cl₂-C₆H₃) | 212 (× ½ NDS) |
| 4-O-(4-Cl-C₆H₄) | -CH₂-C₆H₄-NO₂ | 203 |
| 4-O-(4-NO₂-C₆H₄) | -CH₂-CH=CH₂ | 135 |
| 2,4-Cl₂ | -CH₂-C₆H₄-CH₃ | 92 |
| 2,4-Cl₂ | -CH₂-C₆H₄-O-C₆H₅ | viscous oil |

TABLE 1-continued

(IIa)

| $R_n$ | $R^2$ | Melting point (°C.) or refractive index |
|---|---|---|
| 4-O-C₆H₄-Cl | -CH₂-C₆H₄-O-C₆H₅ | 216 (× ½ NDS) |
| 4-O-C₆H₄-Cl | -CH₂-C₆H₄-CH₃ | 214 (× ½ NDS) |

NOTE:
NDS = 1,5-naphthalenedisulphonic acid

TABLE 2

(IIb)

| $R_n$ | $R^4$ | Melting point (°C.) |
|---|---|---|
| 2,4-Cl₂ | C(CH₃)₃ | 149-51 (× HNO₃) |
| 2,4-Cl₂ | CH₃ | 92-96 |
| 2,4-Cl₂ | —NHCH₃ | 204 |
| 2,4-Cl₂ | —N(CH₃)₂ | 140 |
| 2,4-Cl₂ | C₂H₅ | 156 (× ½ NDS) |
| 2,4-Cl₂ | CH₂Cl | 227 (× ½ NDS) |
| 4-C₆H₄-Cl | CH₃ | 123 |
| 2,4-Cl₂ | -C₆H₄-Cl | 174 (× ½ NDS) |
| 4-O-C₆H₄-Cl | CH₃ | 150 (× HNO₃) |
| 2,4-Cl₂ | —NH—C₆H₅ | 143 |
| 2,4-Cl₂ | —N(CH₃)COCH₃ | 120 |
| 4-C₆H₄-Cl | —NHCH₃ | 180 |
| 2,4-Cl₂ | —NH—C₆H₃Cl₂ (3,4) | 205 (× ½ NDS) |
| 2,4-Cl₂ | NH₂ | 164 |
| 2,4-Cl₂ | —NH—C₆H₃Cl₂ (3,4) | 125 |

TABLE 2-continued

(IIb)

| $R_n$ | $R^4$ | Melting point (°C.) |
|---|---|---|
| 4-C₆H₄-Cl | C(CH₃)₃ | 121 |
| 4-C₆H₄-Cl | —NH—C₆H₅ | 170 (decomposition) |
| 4-Cl | CH₃ | 90-92 |
| 4-Cl | C(CH₃)₃ | 135-136 |
| 4-Cl | —NH—CH₃ | 177-180 |
| 4-C₆H₄-Cl | —NH—C₆H₃Cl₂ (2,5) | 116-126 |
| 4-Cl | —N(CH₃)COCH₃ | 155-158 (× HCl) |
| 2,4-Cl₂ | H | 170-175 (× HCl) |
| 2,4-Cl₂ | CHCl₂ | 128-130 |
| 4-Cl | —NH—C₆H₃Cl₂ | 180-185 |

TABLE 3

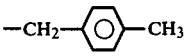

(IIc)

| $R_n$ | $R^3$ | m | Melting point (°C.) |
|---|---|---|---|
| 4-C₆H₄-Cl | -C₆H₄-Cl | 0 | 144 (decomposition) (× HNO₃) |
| 4-C₆H₄-Cl | -C₆H₄-Cl | 1 | |
| 4-C₆H₄-Cl | -C₆H₄-Cl | 2 | |
| 2,4-Cl₂ | -C₆H₄-Cl | 0 | 158 (decomposition) (× HNO₃) |
| 2,4-Cl₂ | -C₆H₄-Cl | 1 | |
| 2,4-Cl₂ | -C₆H₄-Cl | 2 | |

TABLE 3-continued

| $R_n$ | $R^3$ | m | Melting point (°C.) |
|---|---|---|---|
| 4-O-⟨C₆H₄⟩-Cl | -⟨C₆H₄⟩-Cl | 0 | 135 (decomposition) (× HNO₃) |
| 4-O-⟨C₆H₄⟩-Cl | -⟨C₆H₄⟩-Cl | 1 | |
| 4-O-⟨C₆H₄⟩-Cl | -⟨C₆H₄⟩-Cl | 2 | |
| 2,4-Cl₂ | -⟨C₆H₄⟩-C(CH₃)₃ | 0 | 210 (× ½ NDS) |
| 2,4-Cl₂ | -⟨C₆Cl₅⟩ | 0 | 182 (× HNO₃) |
| 2,4-Cl₂ | H | 0 | 147-150 (× HCl) |

The metal salts of the formula (III) required are generally known, readily available compounds.

Possible diluents for the reaction according to the invention are water and all inert organic solvents, especially alcohols, such as methanol and ethanol, ketones, such as acetone or ethyl methyl ketone, and ethers, such as diethyl ether and dioxane.

The reaction temperatures can be varied within a relatively wide range. In general, the reaction is carried out at from 0° to 40° C., preferably at from 15° to 30° C.

In carrying out the process according to the invention, the stoichiometric amount (depending on the oxidation state of the metal) of the compound of the formula (II) is employed per mole of the metal salt (III). These ratios can be exceeded by up to 20 mole % without entailing a substantial decrease in yield. The reaction mixture is worked up in a manner which is customary for organic compounds and which is generally known, for example by filtering off the complex which has precipitated and purifying it by recrystallization, for example from alcohol.

The active compounds according to the invention exhibit a powerful fungitoxic action. They do not damage crop plants in the concentrations required for combating fungi. For these reasons, they are suitable for use as plant protection agents for combating fungi. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens. They display a particularly good activity against parasitic fungi on above-ground parts of plants.

As plant protection agents, the active compounds according to the invention can be employed particularly successfully for combating species of Venturia, such as against the pathogen of apple scab (*Fusicladium dendriticum*), for combating powdery mildew fungi, for example for combating powdery mildew of apples (*Podosphaera leucotricha*) and powdery mildew of cereals, and also against other cereal diseases.

The partially systemic action of the compounds should be singled out particularly. Thus, it proves possible to protect plants against fungal infection by supplying the active compound to the above-ground parts of the plant through the soil and the root.

As plant protection agents, the active compounds according to the invention can be used for the treatment of seed or the treatment of soil, and for the treatment of above-ground parts of plants.

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylene or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

The active compounds according to the invention can be present in the formulations as a mixture with other active compounds, such as fungicides, insecticides, acaricides, nematicides, herbicides, bird repellents, growth factors, plant nutrients and agents for improving soil structure.

The formulations in general contain from 0.1 to 95 percent by weight of active compound, preferably from 0.5 to 90 percent.

The active compounds can be used as such, as their formulations or as the use forms prepared therefrom by further dilution, such as ready-to-use solutions, emulsions, suspensions, powders, pastes and granules. They may be used in the customary manner, for example by watering, spraying, atomising, dusting, scattering, dry dressing, moist dressing, wet dressing, slurry dressing or encrusting.

Especially when used as leaf fungicides, the active compound concentrations in the use forms can be varied within a fairly wide range. They are, in general, from 0.1 to 0.00001 percent by weight, preferably from 0.05 to 0.0001 percent.

For the treatment of seed, amounts of active compound of 0.001 to 50 g per kilogram of seed, preferably 0.01 to 10 g, are generally employed.

For the treatment of soil, amounts of active compound of 1 to 1,000 g per cubic meter of soil, preferably 10 to 200 g, are generally employed.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel complexes is shown in the following illustrative examples:

EXAMPLE 1

(a)

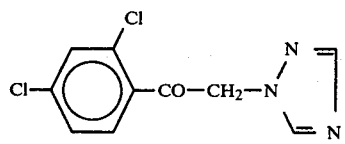

269 g (1 mol) of ω-bromo-2,4-dichloroacetophenone were dissolved in 250 ml of acetonitrile. This solution was added dropwise to a suspension, boiling under reflux, of 69 g (1 mol) of 1,2,4-triazole and 150 g of potassium carbonate in 2 liters of acetonitrile. After heating the mixture under reflux for 20 hours, the cooled suspension was filtered, the filtrate was freed from the solvent, the residue was taken up in acetic acid and the acetic acid solution was washed with water, dried over sodium sulphate and freed from the solvent. The ethyl acetate residue crystallized out on adding isopropanol. After recrystallizing the reaction product from ligroin/isopropanol, 154 g (60% of theory) of ω-(1,2,4-triazol-1-yl)-2,4-dichloroacetophenone of melting point 117° C. were obtained.

(b)

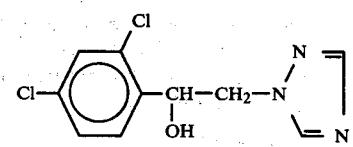

25.6 g (0.1 mol) of ω-(1,2,4-triazol-1-yl)-2,4-dichloroacetophenone were dissolved in 300 ml of methanol, and 4 g (0.1 mol) of sodium borohydride were added in portions at 5° to 10° C., whilst stirring. The mixture was then stirred for a further hour at room temperature and was heated to the boil for one hour. After distilling off the solvent, the residue was heated for a short time with 200 ml of water and 40 ml of concentrated hydrochloric acid. After the reaction mixture had been rendered alkaline with sodium hydroxide solution the solid reaction product could be filtered off. After recrystallising from ligroin/isopropanol, 21.3 g (82% of theory) of 1-hydroxy-1-(2,4-dichlorophenyl)-2-(1,2,4-triazol-1-yl)-ethane of melting point 90° C. were obtained.

(c)

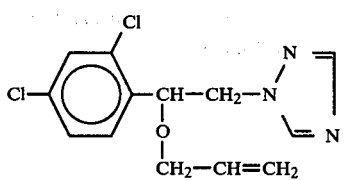

25.7 g (0.1 mol) of 1-hydroxy-1-(2,4-dichlorophenyl)-2-(1,2,4-triazol-1-yl)-ethane were dissolved in 125 ml of dioxane and the solution was added dropwise to a suspension of 4 g of 80% pure sodium hydride in 150 ml of dioxane, while stirring. Thereafter, the mixture was heated under reflux for one hour. After cooling, 22.1 g (0.1 mol) of allyl bromide were added at room temperature to the sodium salt thus obtained. The mixture was then heated under reflux for 8 hours, was allowed to cool and was concentrated by distilling off the solvent. Water and methylene chloride were added to the residue and the organic phase was separated off, dried over sodium sulphate and concentrated. 29.3 g of 1-(2,4-dichlorophenyl)-2-(1,2,4-triazol-1-yl)-ethyl allyl ether having a refractive index $n_D^{22}$ of 1.545 remained, the yield being virtually quantitative.

(d)

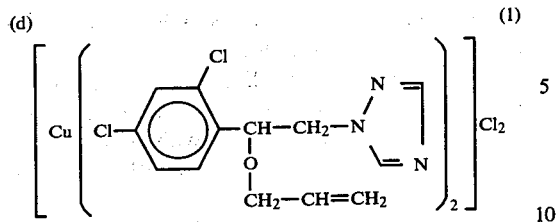

4.25 g (0.025 mol) of copper dichloride (CuCl$_2$.2H$_2$O) were dissolved in 40 ml of water and the solution was added dropwise to 14.9 g (0.05 mol) of 1-(2,4-dichlorophenyl)-2-(1,2,4-triazol-1-yl)-ethyl allyl ether, dissolved in 100 ml of ethanol, whilst stirring. After stirring the mixture at room temperature for three hours, the solid was filtered off, washed with diethyl ether and dried. This gave 13.5 g (75% of theory) of bis-[1-(2,4-dichlorophenyl)-2-(1,2,4-triazol-1-yl)-ethyl allyl ether]-copper-(II) chloride of melting point 158°–160° C.

EXAMPLE 2

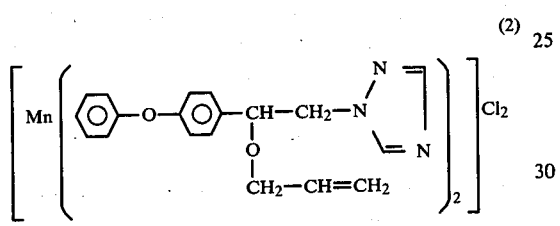

1.7 g (0.0083 mol) of manganese dichloride were dissolved in 40 ml of water and the solution was added dropwise to 5.3 g (0.0166 mol) of 1-(4-phenoxyphenyl)-2-(1,2,4-triazol-1-yl)-ethyl allyl ether, dissolved in 100 ml of ethanol, while stirring. The mixture was stirred at room temperature for 1.5 hours. The oil which had separated out was decanted off and triturated with petroleum ether, whereupon it crystallized completely. The solid was filtered off and dried. This gave 5.5 g (87% of theory) of bis-[1-(4-phenoxyphenyl)-2-(1,2,4-triazol-1-yl)-ethyl allyl ether]-manganese(II) chloride of melting point 180°–200° C.

EXAMPLE 3

(a)

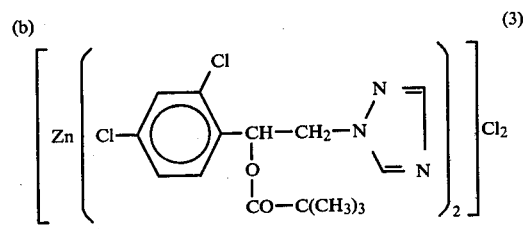

25.8 g (0.1 mol) of 1-(2,4-dichlorophenyl)-1-hydroxy-2-(1,2,4-triazol-1-yl)-ethane were dissolved in 200 ml of dioxane and the solution was added dropwise to a mixture of 6 g of 80% pure sodium hydride and 100 ml of dioxane while stirring. Thereafter, the mixture was heated under reflux for about ½ hour. After cooling, 24 g (0.2 mol) of trimethylacetyl chloride in 100 ml of dioxane were added dropwise at room temperature to the sodium salt thus obtained. The mixture was stirred at room temperature overnight and concentrated by distilling off the solvent in vacuo and the residue was taken up in chloroform. The chloroform solution was washed with water, dried over sodium sulphate and concentrated again. The residue could be further reacted direct.

(b)

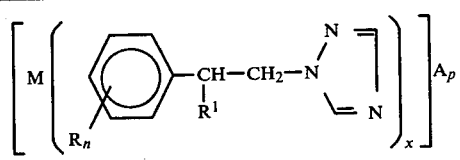

3.5 g (0.025 mol) of zinc dichloride were dissolved in 40 ml of water and the solution was added dropwise to 17 g (0.05 mol) of 1-(2,4-dichlorophenyl)-1-trimethylacetoxy-2-(1,2,4-triazol-1-yl)-ethane, dissolved in 100 ml of ethanol, whilst stirring. After stirring the mixture at room temperature for three hours, the solid was filtered off and dried. This gave 13.1 g (72% of theory) of bis-[1-(2,4-dichlorophenyl)-1-trimethylacetoxy-2-(1,2,4-triazol-1-yl)-ethane]zinc(II) chloride of melting point 160° C.

The compounds in Table 4 which follows were obtained by methods analogous to those of Examples 1 to 3.

TABLE 4

(I)

| Compound No. | M | $R_n$ | $R^1$ | x | $A_p$ | Melting point (°C.) |
|---|---|---|---|---|---|---|
| 4 | Cu | 4-O—⟨◯⟩ | —O—CH$_2$—CH=CH$_2$ | 2 | Cl$_2$ | 90–100 |
| 5 | Sn | 4-O—⟨◯⟩ | —O—CH$_2$—CH=CH$_2$ | 2 | Cl$_4$ | 139–142 |

TABLE 4-continued

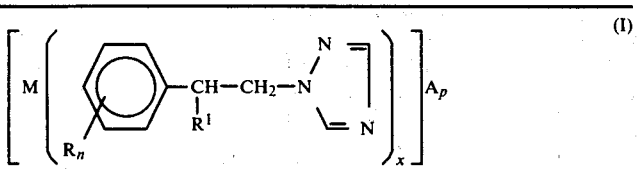

(I)

| Compound No. | M | $R_n$ | $R^1$ | x | $A_p$ | Melting point (°C.) |
|---|---|---|---|---|---|---|
| 6 | Sn | 2,4-$Cl_2$ | $-O-CH_2-CH=CH_2$ | 2 | $Cl_4$ | 126-131 |
| 7 | Cu | 2,4-$Cl_2$ | $-O-CO-C(CH_3)_3$ | 2 | $Cl_2$ | 190-198 |
| 8 | Mn | 2,4-$Cl_2$ | $-O-CH_2-CH=CH_2$ | 2 | $Cl_2$ | 148-152 (× $4H_2O$) |
| 9 | Zn | 2,4-$Cl_2$ | $-O-CH_2-CH=CH_2$ | 2 | $Cl_2$ | 128-130 |

The following compounds of the general formula (I) could be prepared in a corresponding manner.

TABLE 5

| M | $R_n$ | $R^1$ | x | $A_p$ |
|---|---|---|---|---|
| Cu | 2,4-$Cl_2$ | $-S-CH_3$ | 2 | $Cl_2$ |
| Cu | 2,4-$Cl_2$ | $-S-C_2H_5$ | 2 | $Cl_2$ |
| Cu | 2,4-$Cl_2$ | $-S-C_4H_9$ | 2 | $Cl_2$ |
| Cu | 2,4-$Cl_2$ | $-S-CH_2-CH=CH_2$ | 2 | $Cl_2$ |
| Cu | 2,4-$Cl_2$ | $-S-CH_2-\text{(3,4-Cl}_2\text{-phenyl)}$ | 2 | $Cl_2$ |
| Zn | 2,4-$Cl_2$ | $-S-CH_2-\text{(3,4-Cl}_2\text{-phenyl)}$ | 2 | $Cl_2$ |
| Cu | 2,4-$Cl_2$ | $-S-CH_2-\text{(2,6-Cl}_2\text{-phenyl)}$ | 2 | $Cl_2$ |
| Zn | 2,4-$Cl_2$ | $-O-CH_2-\text{(3,4-Cl}_2\text{-phenyl)}$ | 2 | $Cl_2$ |
| Zn | 2,4-$Cl_2$ | $-O-CH_2-\text{(2,6-Cl}_2\text{-phenyl)}$ | 2 | $Cl_2$ |

The fungicidal activity of the compounds of this invention is illustrated by the following biological examples wherein the compounds according to the present invention are each identified by the number (given in brackets) from the examples hereinabove.

The known comparison compounds are identified as follows:

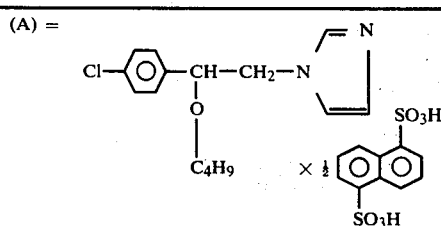

(B) = 
$$\begin{array}{c} CH_2-NHCS \\ | \\ CH_2-NHCS \end{array} \diagdown Zn \diagup \quad \begin{array}{c} \| \\ S \\ \| \\ S \end{array}$$

(C) = Cl—(phenyl)—CH(O-$CH_2-CH=CH_2$)—$CH_2$—N(triazole) × HCl

EXAMPLE 4

Fusicladium test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4-6 leaf stage were sprayed with the spray liquid until dripping wet. The plants remained in a greenhouse for 24 hours at 20° C. and at a relative atmospheric humidity of 70%. They were then inoculated with an aqueous conidium suspension of the apple scab causative organism (Fusicladium dendriticum) and incubated for 18 hours in a humidity chamber at 18°-20° C. and at a relative atmospheric humidity of 100%.

The plants were then brought into a greenhouse again for 14 days.

15 days after inoculation, the infection of the seedlings was determined. The assessment data were converted to percent infection. 0% meant no infection; 100% meant that the plants were totally infected.

The active compounds, the concentrations of the active compounds and the results can be seen from the following table:

TABLE 6

Fusicladium test (apple)/protective

| Active compound | Infection in % at an active compound concentration of 0.0025% |
|---|---|
| (A) | 51 |
| (4) | 26 |
| (2) | 34 |
| (5) | 30 |
| (6) | 34 |
| (7) | 11 |
| (3) | 21 |
| (1) | 15 |
| (9) | 16 |

EXAMPLE 5

Podosphaera test (apple)/protective
  Solvent: 4.7 parts by weight of acetone
  Emulsifier: 0.3 part by weight of alkylaryl polyglycol ether
  Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping wet. The plants remained in a greenhouse for 24 hours at 20° C. and at a relative atmospheric humidity of 70%. They were then inoculated by dusting the conidia of the apple powdery mildew causative organism (*Podosphaera leucotricha*) and placed in a greenhouse at a temperature of 21°–23° C. and at a relative atmospheric humidity of about 70%.

10 days after the inoculation, the infection of the seedlings was determined. The assessment data were converted to % infection. 0% meant no infection; 100% meant that the plants were completely infected.

The active compounds, the concentrations of the active compounds and the results can be seen from the following table:

TABLE 7

Podosphaera test (apple)/protective

| Active compound | Infection in % at an active compound concentration of 0.0025% |
|---|---|
| (A) | 48 |
| (4) | 22 |
| (2) | 29 |
| (5) | 7 |
| (6) | 0 |
| (7) | 0 |
| (3) | 0 |
| (1) | 1 |
| (9) | 0 |

EXAMPLE 6

Shoot Treatment Test/Powdery Mildew of Cereals (Leaf-Destructive Mycosis)/Protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. *hordei*.

After 6 days' dwell time of the plants at a temperature of 21°–22° C. and 80–90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

The active compounds, active compound concentrations in the spray liquor and degrees of infection can be seen from the table which follows:

TABLE 8

Shoot treatment test/powdery mildew of cereals/protective

| Active compounds | Active compound concentration in the spray liquor in % by weight | Infection in % of the untreated control |
|---|---|---|
| untreated | — | 100 |
| (B) | 0.025 | 100 |
| (4) | 0.025 | 12.5 |
| (2) | 0.025 | 8.8 |
| (5) | 0.025 | 3.8 |
| (6) | 0.025 | 0.0 |
| (7) | 0.025 | 0.0 |
| (3) | 0.025 | 0.0 |
| (8) | 0.025 | 0.0 |
| (1) | 0.025 | 0.0 |
| (9) | 0.025 | 0.0 |

EXAMPLE 7

Powdery Mildew of Barley (*Erysiphe graminis* var. *hordei*) (Fungal Disease of Cereal Shoots)/Systemic The active compound was used as a pulverulent seed treatment agent. This was prepared by extending the particular active compound with a mixture of equal parts by weight of talc and kieselguhr to give a finely pulverulent mixture of the desired concentration of active compound.

For the treatment of seed, barley seed was shaken with the extended active compound in a closed glass bottle. The seed was sown at the rate of 3 × 12 grains in flowerpots, 2 cm deep in a mixture of one part by volume of Fruhstorfer standard soil and one part by volume of quartz sand. The germination and emergence took place under favorable conditions in a greenhouse. 7 days after sowing, when the barley plants had developed their first leaf, they were dusted with fresh spores of *Erysiphe graminis* var. *hordei* and grown on at 21°–22° C. and 80–90% relative atmospheric humidity and 16 hours' exposure to light. The typical mildew pustules formed on the leaves over the course of 6 days.

The degree of infection was expressed as a percentage of the infection of the untreated control plants. Thus, 0% denoted no infection and 100% denoted the same degree of infection as in the case of the untreated control. The more active the compound, the lower was the degree of mildew infection.

The active compounds and concentrations of active compound in the seed treatment agent, as well as the amount used of the latter, and the percentage infection with mildew can be seen from the table which follows:

TABLE 9

Powdery mildew of barley test (*Erysiphe graminis* var. *hordei*) systemic

| Active compounds | Active compound concentration in the dressing in % by weight | Amount of dressing used in g/kg of seed | Infection in % of the untreated control |
|---|---|---|---|
| no dressing | — | — | 100 |
| (B) | 25 | 10 | 100 |
| (6) | 25 | 10 | 0.0 |
| (7) | 25 | 10 | 0.0 |
| (3) | 25 | 10 | 0.0 |
| (8) | 25 | 10 | 0.0 |
| (1) | 25 | 10 | 0.0 |
| (9) | 25 | 10 | 0.0 |

EXAMPLE 8

Mycelium Growth Test

Nutrient medium used:
 20 parts by weight of agar-agar
 200 parts by weight of potato decoction
 5 parts by weight of malt
 15 parts by weight of dextrose
 5 parts by weight of peptone
 2 parts by weight of disodium hydrogen phosphate
 0.3 part by weight of calcium nitrate
Composition of the solvent mixture:
 0.19 part by weight of acetone or DMF
 0.01 part by weight of emulsifier (alkylaryl polyglycol ether)
 1.80 parts by weight of water
Ratio of solvent mixture to nutrient medium:
 2 parts by weight of solvent mixture
 100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified, the plates were inoculated with the species of organisms stated in the table and incubated at about 21° C.

Evaluation was carried out after 4–10 days, dependent upon the speed of growth of the organisms. When evaluation was carried out the radial growth of the organism on the treated nutrient media was compared with the growth on the control nutrient medium. In the evaluation of the organism growth, the following characteristic values were used:
 1 no growth
 up to 3 very strong inhibition of growth
 up to 5 medium inhibition of growth
 up to 7 slight inhibition of growth
 9 growth equal to that of untreated control.

The active compounds, the active compound concentrations and the results can be seen from the following table:

TABLE 10

Mycelium growth test

| Active compound | Active compound concentration in ppm | Colletotrichum coffeanum | Botrytis cinerea | Verticillium alboatrum | Phytophthora cactorum | Pyricularia oryzae | Helminthosporum gramineum |
|---|---|---|---|---|---|---|---|
| (C) | 10 | 9 | 5 | 5 | 9 | 5 | 5 |
| (1) | 10 | 3 | — | 2 | 2 | 1 | 2 |
| (6) | 10 | — | 3 | 1 | — | 1 | 2 |
| (9) | 10 | 5 | — | 1 | 1 | 1 | 2 |

It will be appreciated that the instant specification and examples are set forth by way of illustration and not limitation, and that various modifications and changes may be made without departing from the spirit and scope of the present invention.

What we claim is:

1. A metal salt complex of a 1-phenyl-2-(1,2,4-triazol-1-yl)-ethane of the formula

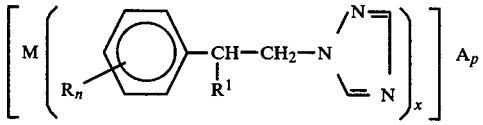

in which
R is halogen, nitro, cyano, alkyl with 1 to 4 carbon atoms, alkylsulphonyl with 1 to 4 carbon atoms, alkoxy with 1 or 2 carbon atoms, alkylthio with 1 to 2 carbon atoms, halogenoalkyl with up to 4 carbon atoms and up to 5 halogen atoms, phenyl, phenoxy, or phenyl or phenoxy carrying at least one substituent selected from halogen, cyano, nitro and halogenoalkyl with up to 2 carbon atoms and up to 3 independent halogen atoms;

$R^1$ is —O—$R^2$, —S(O)$_m$—$R^3$ or —O—CO—$R^4$;

$R^2$ is alkyl, alkenyl or alkynyl each with up to 4 carbon atoms; cycloalkyl with 5 to 7 carbon atoms; phenyl, naphthyl, or phenylalkyl, naphthylalkyl, phenylalkenyl or naphthylalkenyl each with up to 4 carbon atoms in the alkyl or alkenyl part, the phenyl or naphthyl moieties optionally being substituted by halogen, cyano, nitro, amino, alkyl with 1 to 4 carbon atoms, halogenoalkyl with up to 2 carbon atoms and up to 3 independent halogen atoms, phenoxy or halophenoxy;

$R^3$ is hydrogen; alkyl, alkenyl or alkynyl each with up to 4 carbon atoms; cycloalkyl with 5 to 7 carbon atoms; phenyl, naphthyl, phenylalkyl, naphthylalkyl, phenylalkenyl or naphthylalkenyl, each of the four last-mentioned groups having up to 4 carbon atoms in the alkyl or alkenyl part, the phenyl or naphthyl moieties optionally being substituted by halogen, cyano, nitro, amino, alkyl with 1 to 4 carbon atoms, halogenoalkyl with up to 2 carbon atoms and up to 3 independent halogen atoms, phenoxy or halophenoxy;

R⁴ is alkyl, alkenyl or alkynyl each with up to 4 carbon atoms; cycloalkyl with 5 to 7 carbon atoms; phenyl, naphthyl, or phenylalkyl, naphthylalkyl, phenylalkenyl, or naphthylalkenyl, each having up to 4 carbon atoms in the alkyl or alkenyl part, the phenyl or naphthyl moieties optionally being substituted by halogen, cyano, nitro, amino, alkyl with 1 to 4 carbon atoms, halogenoalkyl with up to 2 carbon atoms and up to 3 independent halogen atoms, phenoxy or halophenoxy; halogenoalkyl with 1 to 2 carbon atoms and 1 to 5 halogen atoms; phenoxyalkyl which has 1 or 2 carbon atoms in the alkyl part and optionally substituted in the phenyl part by halogen, amino, cyano, nitro or alkyl with 1 to 2 carbon atoms; amino; alkylamino, dialkylamino or alkyl-alkylcarbonylamino each with 1 to 4 carbon atoms in each alkyl part; or phenylamino which is optionally substituted by halogen, nitro and cyano;

M is copper, zinc, manganese, magnesium, tin, iron or nickel,

A is an anion of an inorganic acid, n represents 0, 1, 2, 3, 4 or 5, m represents 0, 1 or 2, p represents 1, 2, 3, 4, 5 or 6, and x represents 1, 2, 3 or 4.

2. A complex according to claim 1, wherein such complex is a bis-[1-(2,4-dichlorophenyl)-2-(1,2,4-triazol-1-yl)-ethyl allyl ether]-copper (II) halide of the formula

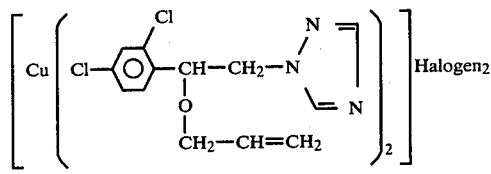

3. A complex according to claim 1, wherein such complex is a tetrakis-[1-(2,4-dichlorophenyl)-2-(1,2,4-triazol-1-yl)-ethyl allyl ether]-tin (IV) halide of the formula

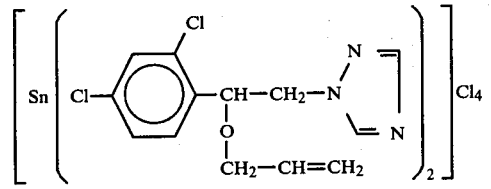

4. A complex according to claim 1, wherein such complex is a bis-[1-(2,4-dichlorophenyl)-2-(1,2,4-triazol-1-yl)-ethyl tert.-butyl-carboxylate]-copper (II) halide of the formula

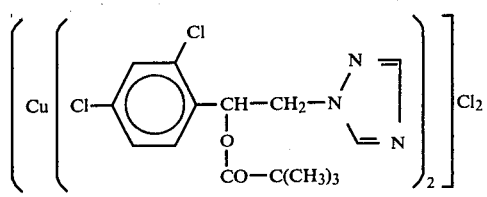

5. A complex according to claim 1, wherein such complex is a bis-[1-(2,4-dichlorophenyl)-2-(1,2,4-triazol-1-yl)-ethyl allyl ether]-manganese (II) halide of the formula

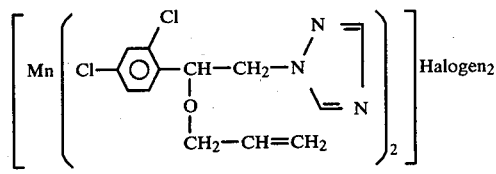

6. A complex according to claim 1, wherein such complex is a bis-[1-(2,4-dichlorophenyl)-2-(1,2,4-triazol-1-yl)-ethyl allyl ether]-zinc (II) halide of the formula

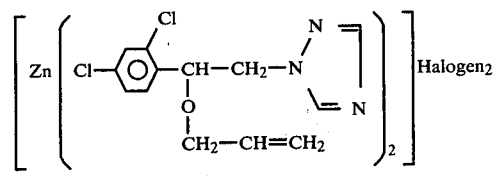

7. A fungicidal composition containing as active ingredient a fungicidally effective amount of a complex according to claim 1 in admixture with a diluent.

8. A method of combating fungi which comprises applying to the fungi, or to a habitat thereof, a fungicidally effective amount of a complex according to claim 1.

9. The method according to claim 8 in which said complex is a halide of
bis-[1-(2,4-dichlorophenyl)-2-(1,2,4-triazol-1-yl)-ethyl allyl ether]-copper (II),
tetrakis-[1-(2,4-dichlorophenyl)-2-(1,2,4-triazol-1-yl)-ethyl allyl ether]-tin (IV),
bis-[1-(2,4-dichlorophenyl)-2-(1,2,4-triazol-1-yl)-ethyl tert.-butyl-carboxylate]-copper (II),
bis-[1-(2,4-dichlorophenyl)-2-(1,2,4-triazol-1-yl)-ethyl allyl ether]-manganese (II), or
bis-[1-(2,4-dichlorophenyl)-2-(1,2,4-triazol-1-yl)-ethyl allyl ether]-zinc (II).

10. A complex according to claim 1, in which
A is a halide, nitrate, sulfate or phosphate anion,
n is 0,1,2 or 3 and
p is 1,2,3 or 4.

* * * * *